(12) United States Patent
Tang

(10) Patent No.: US 12,025,904 B1
(45) Date of Patent: Jul. 2, 2024

(54) CAMERA ASSEMBLY OF VISUAL EARPICK

(71) Applicant: Songshu Tang, Shaoyang (CN)

(72) Inventor: Songshu Tang, Shaoyang (CN)

( * ) Notice: Subject to any disclaimer, the term of this patent is extended or adjusted under 35 U.S.C. 154(b) by 0 days.

(21) Appl. No.: 18/590,555

(22) Filed: Feb. 28, 2024

(51) Int. Cl.
  *G03B 17/12* (2021.01)
  *A61F 11/00* (2022.01)

(52) U.S. Cl.
  CPC ............ *G03B 17/12* (2013.01); *A61F 11/006* (2013.01); *G03B 2217/002* (2013.01)

(58) Field of Classification Search
  None
  See application file for complete search history.

(56) References Cited

U.S. PATENT DOCUMENTS

| | | | |
|---|---|---|---|
| 6,699,178 B1 | 3/2004 | Koda | |
| 2004/0249244 A1* | 12/2004 | Koda | A61F 11/006 600/200 |
| 2024/0033128 A1 | 2/2024 | Qin et al. | |

FOREIGN PATENT DOCUMENTS

| | | | | |
|---|---|---|---|---|
| CN | 202027789 U | * | 11/2011 | |
| CN | 112294534 A | * | 2/2021 | ............ A61F 11/006 |
| CN | 114053025 A | * | 2/2022 | |
| CN | 217216722 U | * | 8/2022 | |
| CN | 217216722 U | | 8/2022 | |
| CN | 218075436 U | * | 12/2022 | |
| CN | 218075436 U | | 12/2022 | |
| WO | WO-2022100669 A1 | * | 5/2022 | ......... A45D 26/0076 |

* cited by examiner

*Primary Examiner* — Clayton E. LaBalle
*Assistant Examiner* — Diana Hancock

(57) ABSTRACT

The present utility model discloses a camera assembly of a visual earpick, which comprises: a sleeve, a camera module and a light-emitting assembly, wherein a front end of the camera module is provided with a first convex step, and the light-emitting assembly is arranged on the first convex step; the camera module comprises a lens and a circuit board assembly, the circuit board assembly comprises a flexible circuit board, a fixed plate and a support plate, the fixed plate is arranged below the lens, one end of the support plate is vertically fixed below the fixed plate, a clamping groove is arranged at a lower part of an inner side of the sleeve, and the other end of the support plate is at least partially inserted into the clamping groove to limit and fix the circuit board assembly.

10 Claims, 3 Drawing Sheets

CAMERA ASSEMBLY OF VISUAL EARPICK

TECHNICAL FIELD

The present utility model relates to the technical field of earpicks, and in particular, to a camera assembly of a visual earpick.

BACKGROUND

An earpick is one of the commonly used ear cleaning tools that enter an ear canal through a front end to clean the earwax inside the ear canal. When users use the earpick by themselves, the users cannot observe the internal conditions of the ear canal, and the ear canal is easily scratched during operation, making the earpick inconvenient to use. Currently, there is an ear picking device on the market that can integrate a camera and an earpick to visualize the internal conditions of the ear. However, a camera module of this ear-picking device cannot be stably fixed to the earpick and is prone to falling into the ear canal. Therefore, it is desirable to provide an earpick assembly that can observe the internal structure of the ear canal and stably fix a camera assembly on the earpick.

SUMMARY

A primary objective of the present utility model is to provide a camera assembly of a visual earpick, which aims to solve the problem that the inside of an ear canal cannot be observed by the existing earpick.

To achieve the objective, the present utility model provides a camera assembly of a visual earpick, which comprises: a sleeve, a camera module and a light-emitting assembly, wherein the sleeve is provided with a through hole for the camera module to pass through; a front end of the camera module is provided with a first convex step, and the light-emitting assembly is arranged on the first convex step; the camera module comprises a lens and a circuit board assembly electrically connected to the lens, the circuit board assembly comprises a flexible circuit board, a fixed plate and a support plate for supporting the flexible circuit board, the fixed plate is arranged below the lens, one end of the support plate is vertically fixed below the fixed plate, a clamping groove is arranged at a lower part of an inner side of the sleeve, and the other end of the support plate is at least partially inserted into the clamping groove to limit and fix the circuit board assembly.

Optionally, the support plate is in an inverted T-shaped structure, two clamping grooves are symmetrically provided, and two lugs of the support plate are inserted into the clamping grooves.

Optionally, a limiting part for abutting against the camera module or the light-emitting module is provided on an inner side of a front end of the through hole.

Optionally, the clamping groove is provided at a tail end of the sleeve.

Optionally, the support plate is fixed below the fixed plate by glue.

Optionally, the camera assembly of the visual earpick further comprises an earpick head arranged at a front end of the sleeve.

Optionally, a second annular convex step is formed at the front end of the sleeve, and the earpick head is detachably sleeved on the second annular convex step.

Optionally, the sleeve and the earpick head are integrally provided.

Optionally, the camera assembly of the visual earpick further comprises a silicone sleeve detachably arranged on the earpick head and/or the sleeve.

Optionally, the light-emitting assembly comprises a lamp panel arranged around the first convex step and lamp beads arranged on the lamp panel, and the lamp panel is electrically connected to the circuit board assembly.

According to the camera assembly of the visual earpick provided by the present utility model, the camera module is arranged in the through hole of the sleeve, and the light-emitting assembly is fixed on the first convex step of the camera module, so that the ear canal can be illuminated and photographed by connecting a handle during use; meanwhile, the fixed plate is fixed with the lens, and the support plate is vertically arranged below the fixed plate, so that the camera assembly can be assembled in the sleeve conveniently; and the support plate is inserted into the clamping groove to fix the circuit board assembly, so that the stability of assembly is ensured, the camera assembly is prevented from falling off when being used in an ear canal, and the use safety is ensured.

BRIEF DESCRIPTION OF DRAWINGS

To more clearly illustrate the technical solutions in the embodiments of the present utility model or in the prior art, the drawings required to be used in the description of the embodiments or the prior art are briefly introduced below. It is obvious that the drawings in the description below are only some embodiments of the present utility model, and those of ordinary skill in the art can obtain other drawings according to structures illustrated in these drawings without creative efforts.

DESCRIPTIONS OF REFERENCE NUMERALS

Figure 1:
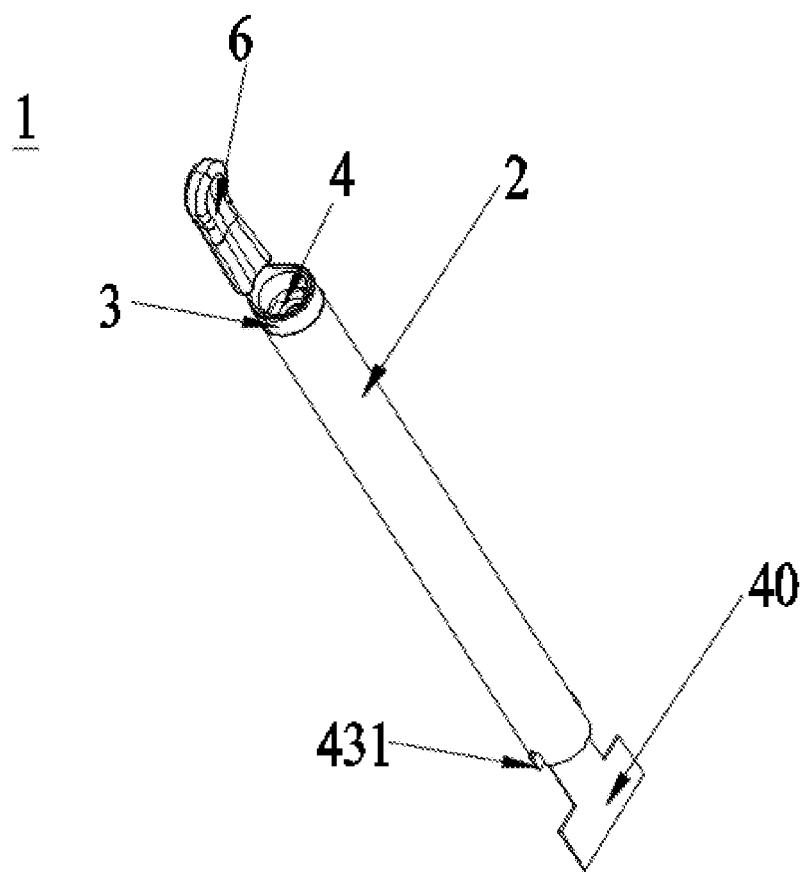
FIG. 1 is a schematic diagram of a state of a camera assembly of a visual earpick according to the present utility model.

| Camera assembly | 1 | Lamp panel | 211 |
| Sleeve | 2 | Lamp bead | 212 |
| Earpick head | 3 | First convex step | 22 |
| Camera module | 4 | Circuit board assembly | 40 |
| Clamping groove | 5 | Lens | 41 |
| Silicone sleeve | 6 | Flexible circuit board | 42 |
| Through hole | 201 | Support plate | 43 |
| Second annular convex step | 202 | Lug | 431 |
| Limiting part | 203 | Fixed plate | 44 |
| Light-emitting assembly | 21 | | |

The realization of the objectives, the functional features, and the advantages of the present utility model will be further explained in conjunction with the embodiments and with reference to the drawings.

DETAILED DESCRIPTION OF EMBODIMENTS

The technical solutions in the embodiments of the present utility model will be clearly and completely described below with reference to the drawings in the embodiments of the present utility model. It is apparent that the described embodiments are only some, but not all, embodiments of the present utility model. Based on the embodiments of the present utility model, all other embodiments obtained by those of ordinary skill in the art without creative efforts fall within the protection scope of the present utility model.

It should be noted that, if directional indications (such as upper, lower, left, right, front and rear) are involved in the embodiments of the present utility model, the directional indications are only used to explain the relative positional relationships, the motion situations and the like between individual components under a certain pose (as shown in the drawings), and if the certain pose is changed, the directional indications are changed accordingly.

In addition, if there are descriptions relating to "first", "second" and the like in the embodiments of the present utility model, the descriptions of "first", "second" and the like are for descriptive purposes only and are not to be construed as indicating or implying relative importance thereof or implicitly indicating the quantities of the indicated technical features. Thus, a feature defined by "first" or "second" may explicitly or implicitly include at least one such feature. In addition, "and/or" appearing herein is meant to include three parallel solutions, and taking "A and/or B" as an example, it includes solution A, or solution B, or both solution A and solution B. In addition, the technical solutions among various embodiments may be combined with each other, however, this combination must be based on that it can be realized by those of ordinary skill in the art. When the combination of the technical solutions is contradictory or cannot be realized, such a combination of the technical solutions should not be considered to exist, and is not within the protection scope of the present utility model.

To solve the problem that the inside of an ear canal cannot be observed by an existing earpick, the present utility model provides a camera assembly 1 of a visual earpick, the camera assembly 1 is configured to connect to a handle (not shown in the figure) to form the visual earpick, images of the ear canal are transmitted in real time through the connection of the visual earpick and a mobile terminal, a user can synchronously observe the inside of the ear canal in this process, and the risk of damaging the ear canal in the use process can be reduced.

Figure 2:
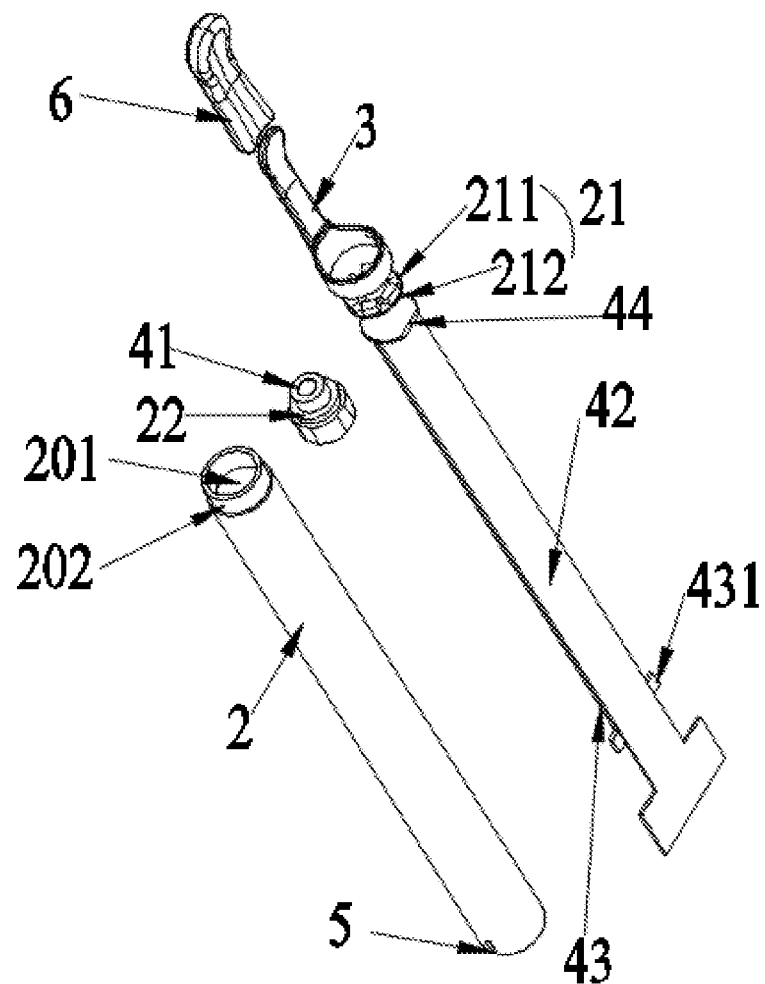
FIG. 2 is a schematic diagram of an exploded state of a camera assembly of a visual earpick according to the present utility model.
Figure 3:
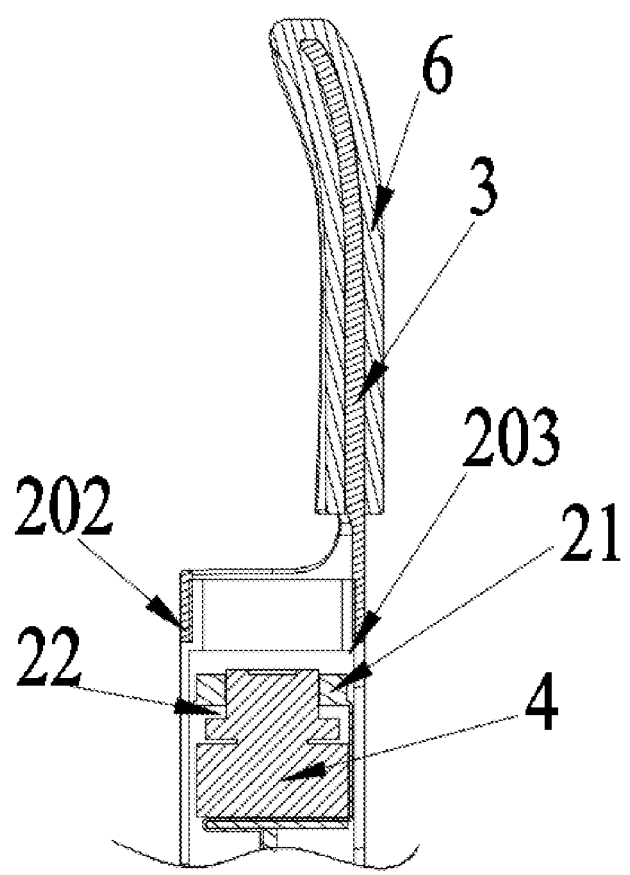
FIG. 3 is a sectional view of a front end of a sleeve of a camera assembly of a visual earpick according to the present utility model.

Specifically, with reference to FIGS. 1 to 3, the camera assembly 1 of the visual earpick comprises a sleeve 2, a camera module 4 and a light-emitting assembly 21, and the sleeve 2 is provided with a through hole 201 for the camera module 4 to pass through. The light-emitting assembly 21 is electrically connected to the camera module 4, a front end of the camera module 4 is provided with a first convex step 22, and the light-emitting assembly 21 is fixed on the first convex step 22 in a surrounding mode. The light-emitting assembly 21 is configured to illuminate the inside of the ear canal so as to facilitate the camera module 4 to take a picture, and the first convex step 22 is used for enabling the light-emitting assembly to surround the camera module 4 so as to provide a better illumination effect.

The camera module 4 comprises a lens 41 and a circuit board assembly 40 electrically connected to the lens 41, wherein the lens 41 is a photosensitive lens; the circuit board assembly 40 comprises a flexible circuit board 42, a fixed plate 44 and a support plate 43 for fixing the flexible circuit board 42, wherein the fixed plate 44 and the support plate 43 are each configured to fix with the flexible circuit board 42, so as to ensure the mounting of the flexible circuit board 42 in the through hole 201; and the fixed plate 44 is arranged below the lens 41 and is configured to fix the lens 41 and the circuit board assembly 40, one end of the support plate 43 is vertically fixed below the fixed plate 44 to ensure that the circuit board assembly 40 is mounted in the through hole 201, and simultaneously ensure that a size of the whole camera assembly 1 is not too large to affect the use in the ear canal. The light-emitting assembly 21 and the lens 41 are electrically connected to the circuit board assembly 40. The lens 41 and the circuit board are based on the prior art and are not improved.

With further reference to FIG. 3, in the camera assembly 1 of the visual earpick of the present utility model, a clamping groove 5 is arranged at a lower part of an inner side of the sleeve 2, the other end of the support plate 43 is at least partially inserted into the clamping groove 5 to limit and fix the circuit board assembly 40, the camera module 4 is effectively fixed and limited by the snap-fitting of the support plate 43 and the clamping groove 5, and the risk that the camera module 4 falls into the ear canal in the use process is reduced.

Further, in the present utility model, the support plate 43 is in an inverted T-shaped structure, two clamping grooves 5 are symmetrically provided, and two lugs 431 of the support plate 43 are inserted into the clamping grooves 5.

To facilitate the assembly of the camera module 4, the clamping groove 5 is arranged at a tail end of the sleeve 2, that is, one end of the clamping groove 5 is flush with an edge of the sleeve 2. In other embodiments, the clamping groove 5 can also be arranged inside the lower part of the sleeve 2.

With reference to FIG. 3, to further ensure that the camera module 4 does not fall into the ear canal, a limiting part 203 may be provided at an opening at a front end of the sleeve 2, and the limiting part 203 is a limiting structure protruding from the inner wall of the sleeve, such as a limiting block or a limiting member. The limiting part 203 is provided such that an outer diameter of the opening is smaller than the camera module 4 or the light-emitting module. Specifically, the camera assembly 1 may be configured such that an outer edge of the light-emitting assembly 21 abuts against the limiting part 203, or a certain gap is reserved between the limiting part 203 and the light-emitting assembly, and when the clamping groove 5 cannot support and limit the camera module 4, the limiting part 203 can prevent the camera module 4 from falling into the ear canal. Alternatively, an inner diameter of the opening of the sleeve 2 can be slightly smaller than the outer diameter of the camera module 4 of the camera assembly 1.

The light-emitting assembly 21 comprises a lamp panel 211 arranged around the first convex step 22, and the lamp panel 211 is provided with lamp beads 212 with a light-emitting surface facing the front end of the sleeve 2. A plurality of lamp beads 212 are preferably provided and uniformly distributed on a peripheral side of the lens 41. The support plate 43 and the fixed plate 44 are generally made of steel plates, and the lens 41 and the fixed plate 44 may be fixed by an adhesive. The fixed plate 44 and the support plate 43 can be fixed by glue, by snap-fitting of a limiting structure provided on a lower side of the fixed plate 44 and a corresponding connecting structure provided on an upper side of the support plate 43, or by a combination of a plurality of manners.

Further, the front end of the sleeve 2 is connected to an earpick head 3 for cleaning inside the ear canal, the earpick head 3 is configured to clean earwax in the ears, and the earpick head 3 can be a spoon-shaped earpick head 3 and can also be a spiral earpick head 3, and the spiral earpick head can be configured to massage or rotationally clean the ear canal. The earpick head 3 can be integrally formed with the camera assembly 1 and can also be provided with a second annular convex step 202 at the front end of the sleeve 2, the earpick head 3 can be detachably sleeved on the second annular convex step 202, and the camera assembly can still extend into the ear canal as a visual assembly when the earpick head 3 is taken down.

Further, with reference to FIG. 1, to ensure the convenience of using the visual earpick, the camera assembly 1 may further comprise a silicone sleeve 6 detachably arranged on the sleeve 2 and/or the earpick head 3, the shape of the silicone sleeve 6 may be adapted to the earpick head 3 and the sleeve 2, and the silicone sleeve 6 may be softer than the earpick head 3, so as to better protect the ear canal and also protect the sleeve 2; and meanwhile, the silicone sleeve 6 can be replaced, so that different people can use the earpick, and sanitation is guaranteed.

The above mentioned contents are only optional embodiments of the present utility model and are not intended to limit the patent scope of the present utility model, and under the inventive concept of the present utility model, the equivalent structural transformations made by using the contents of the specification and the drawings of the present utility model, or direct/indirect applications to other related technical fields, are all included in the patent protection scope of the present utility model.

The invention claimed is:

1. A camera assembly of a visual earpick, comprising: a sleeve, a camera module and a light-emitting assembly, wherein the sleeve is provided with a through hole for the camera module to pass through; a front end of the camera module is provided with a first convex step, and the light-emitting assembly is arranged on the first convex step; the camera module comprises a lens and a circuit board assembly electrically connected to the lens, the circuit board assembly comprises a flexible circuit board, a fixed plate and a support plate for supporting the flexible circuit board, the fixed plate is arranged below the lens, one end of the support plate is vertically fixed below the fixed plate, a clamping groove is arranged at a lower part of the sleeve, and the other end of the support plate is at least partially inserted into the clamping groove to limit and fix the circuit board assembly.

2. The camera assembly of the visual earpick according to claim 1, wherein the support plate is in an inverted T-shaped structure, two clamping grooves are symmetrically provided, and two lugs of the support plate are inserted into the clamping grooves.

3. The camera assembly of the visual earpick according to claim 2, wherein a limiting part for abutting against the camera module or the light-emitting module is provided on an inner side of a front end of the through hole.

4. The camera assembly of the visual earpick according to claim 3, wherein the light-emitting assembly comprises a lamp panel arranged around the first convex step and lamp beads arranged on the lamp panel, and the lamp panel is electrically connected to the circuit board assembly.

5. The camera assembly of the visual earpick according to claim 2, wherein the clamping groove is provided at a tail end of the sleeve.

6. The camera assembly of the visual earpick according to claim 5, wherein the support plate is fixed below the fixed plate by glue.

7. The camera assembly of the visual earpick according to claim 2, wherein the camera assembly of the visual earpick further comprises an earpick head arranged at a front end of the sleeve.

8. The camera assembly of the visual earpick according to claim 7, wherein a second annular convex step is formed at the front end of the sleeve, and the earpick head is detachably sleeved on the second annular convex step.

9. The camera assembly of the visual earpick according to claim 7, wherein the sleeve and the earpick head are integrally provided.

10. The camera assembly of the visual earpick according to claim 7, wherein the camera assembly further comprises a silicone sleeve detachably arranged on the earpick head and/or the sleeve.

* * * * *